(12) United States Patent
Allegretti et al.

(10) Patent No.: US 9,328,057 B2
(45) Date of Patent: May 3, 2016

(54) CHIRAL ARYLKETONES IN THE TREATMENT OF NEUTROPHIL-DEPENDENT INFLAMMATORY DISEASES

(75) Inventors: Marcello Allegretti, L'Aquila (IT); Riccardo Bertini, L'Aquila (IT); Maria Candida Cesta, L'Aquila (IT); Cinzia Bizzarri, L'Aquila (IT); Francesco Colotta, L'Aquila (IT)

(73) Assignee: DOMPE' FARMACEUTICI S.P.A., Milan (IT)

( * ) Notice: Subject to any disclaimer, the term of this patent is extended or adjusted under 35 U.S.C. 154(b) by 137 days.

(21) Appl. No.: 12/327,767

(22) Filed: Dec. 3, 2008

(65) Prior Publication Data

US 2009/0203652 A1 Aug. 13, 2009

Related U.S. Application Data

(63) Continuation of application No. 10/537,824, filed as application No. PCT/EP03/13946 on Dec. 9, 2003, now abandoned.

(30) Foreign Application Priority Data

Dec. 10, 2002 (EP) ..................... 02027453

(51) Int. Cl.

| | | |
|---|---|---|
| *C07C 317/24* | (2006.01) | |
| *C07C 311/21* | (2006.01) | |
| *C07C 309/65* | (2006.01) | |
| *C07C 271/18* | (2006.01) | |
| *C07C 69/738* | (2006.01) | |
| *C07C 49/782* | (2006.01) | |
| *C07C 49/215* | (2006.01) | |
| *C07C 49/213* | (2006.01) | |
| *C07D 319/06* | (2006.01) | |
| *C07D 213/50* | (2006.01) | |
| *C07D 209/46* | (2006.01) | |
| *A61K 31/12* | (2006.01) | |
| *A61K 31/192* | (2006.01) | |
| *A61K 31/662* | (2006.01) | |
| *A61K 31/10* | (2006.01) | |
| *A61K 31/44* | (2006.01) | |
| *A61P 29/00* | (2006.01) | |
| *C07C 45/56* | (2006.01) | |
| *C07C 45/67* | (2006.01) | |
| *C07F 9/40* | (2006.01) | |

(52) U.S. Cl.
CPC ............ *C07C 69/738* (2013.01); *C07C 45/562* (2013.01); *C07C 45/673* (2013.01); *C07C 45/676* (2013.01); *C07C 49/213* (2013.01); *C07C 49/215* (2013.01); *C07C 49/782* (2013.01); *C07C 271/18* (2013.01); *C07C 309/65* (2013.01); *C07C 311/21* (2013.01); *C07C 317/24* (2013.01); *C07D 209/46* (2013.01); *C07D 213/50* (2013.01); *C07D 319/06* (2013.01); *C07F 9/4059* (2013.01); *C07B 2200/07* (2013.01)

(58) Field of Classification Search
CPC .. C07C 45/562; C07C 317/24; C07C 311/21; C07C 309/65; C07C 271/18; C07C 69/738; C07C 49/782; C07C 49/215; C07C 49/213; C07D 319/06; C07D 213/50; C07D 209/46; C07D 309/65; C07D 271/18; C07D 69/738; C07D 49/782; C07D 49/215; C07D 49/213; A61K 31/12; A61K 31/192; A61K 31/662; A61K 31/10; A61K 31/44; A61P 29/00
See application file for complete search history.

(56) References Cited

U.S. PATENT DOCUMENTS 3,876,648 A 4/1975 Haas et al.
4,151,172 A 4/1979 Ondetti et al.

FOREIGN PATENT DOCUMENTS

| EP | 0511021 | 10/1992 |
|---|---|---|
| JP | 52108949 | 9/1977 |
| JP | 56097249 | 8/1981 |
| JP | 03024023 | 2/1991 |
| JP | 5-286902 A | 11/1993 |
| JP | 05286902 | 11/1993 |

(Continued)

OTHER PUBLICATIONS

Allegretti et al., "2-arylpropionic CXC chemokine receptor 1 ligands as novel noncompetitive cxcl8 inhibitors", J. Med. Chem. 2005, 48, 4312-4331.*
Barnes, P.J., "Mediators of Chronic Obstructive Pulmonary Disease", Pharmacological Reviews, vol. 56, No. 4, p. 515-548.*
McCulloch et al. "Signalling Platforms that Modulate the Inflammatory Response: New Targets for Drug Development", Nature Reviews Drug Discovery (2006), vol. 5, p. 864-876.*
IL8, 2013, http://en.wikipedia.org/wiki/Interleukin_8.*
Database Beilstein, Beilstein Institute for Organic Chemistry, Frankfurt-Main, DE; XP002275017, Database Accession Nos. 1942753, 1943166, 1943612. 1943613, 1945434, 1945435, 1945436, 1945437, 1948204, 1950022, 1968443, 2362885, 2447357, 2451750 (BRN's) & Chim. Ther., vol. 3, 1968, pp. 313-320.

(Continued)

*Primary Examiner* — Sun Jae Yoo
(74) *Attorney, Agent, or Firm* — Steinfl & Bruno LLP

(57) ABSTRACT

The compounds of formula (I):

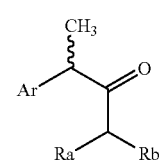

where Ar is an aromatic ring and Ra, Rb, are as defined in the description, are useful in therapy as drugs for the treatment of diseases mediated by infiltrations of neutrophils induced by IL-8, such as psoriasis, rheumatoid arthritis, ulcerative cholitis and for the treatment of damages caused by ischemia and reperfusion.

8 Claims, No Drawings

(56) References Cited

FOREIGN PATENT DOCUMENTS

| WO | WO-00/24710 A | 5/2000 |
|---|---|---|
| WO | WO-01/58852 A | 8/2001 |

OTHER PUBLICATIONS

Database Beilstein, Beilstein Institute for Organic Chemistry, Frankfurt-Main, DE; XP002275018, Database Accession Nos. 1955069, 1958359 (BRN's) & Bull. Soc. Chim. Fr., 1974, pp. 1415-1420.
Database Beilstein, Beilstein Institute for Organic Chemistry, Frankfurt-Main, DE; XP002275019, Database Accession Nos. 2104506, 2451415 (BRN's) & J. Am. Chem. Soc., vol. 103, No. 11, 1981, pp. 3088-3093.
Database Beilstein, Beilstein Institute for Organic Chemistry, Frankfurt-Main, DE; XP002275020, Database Accession No. 3242777 (BRN) & J. Am. Chem. Soc., vol. 81, 1959, pp. 5193-5197.
Database Beilstein, Beilstein Institute for Organic Chemistry, Frankfurt-Main, DE; XP002275021, Database Accession No. 2842765 (BRN) & Acta Chem. Scand., vol. 20, 1966, pp. 2467-2479.
Database Beilstein, Beilstein Institute for Organic Chemistry, Frankfurt-Main, DE, XP002275022, Database Accession Nos. 3033411, 3651979, 3651980 (BRN's) & J. Med. Chem., vol. 33, No. 6, 1990, pp. 1741-1748.
Database Beilstein, Beilstein Institute for Organic Chemistry, Frankfurt-Main, DE; XP002275023, Database Accession No. 4661814 (BRN) & Bull. Chem. Soc. Jpn., vol. 64, No. 11, 1991, pp. 3743-3475.
Database Beilstein, Beilstein Institute for Organic Chemistry, Frankfurt-Main, DE; XP002275024, Database Accession No. 5013506 (BRN) & Tetrahedron Lett., vol. 27, No. 35, 1986, pp. 4175-4176.
Database Beilstein, Beilstein Institute for Organic Chemistry, Frankfurt-Main, DE; XP002275025, Database Accession Nos. 5379213, 5379214 (BRN's) & J. Am. Chem. Soc., vol. 105, No. 5, 1983, pp. 1309-1316.
Database Beilstein, Beilstein Institute for Organic Chemistry, Frankfurt-Main, DE; XP002275026, Database Accession No. 6863126 (BRN) & J. Org. Chem., vol. 50, No. 9, 1985, pp. 1504-1509.
Database Beilstein, Beilstein Institute for Organic Chemistry, Frankfurt-Main, DE; XP002275027, Database Accession No. 6978265 (BRN) Farmaco Ed. Sci., vol. 40, No. 12, 1985, pp. 942-955.
Database Beilstein, Beilstein Institute for Organic Chemistry, Frankfurt-Main, DE; XP002275028, Database Accession No. 7020327 (BRN) & Tetrahedron Asymmetry, vol. 5, No. 9, 1994, pp. 1763-1780.
Database Beilstein, Beilstein Institute for Organic Chemistry, Frankfurt-Main, DE; XP4981202 (BRN) Synth Commun., vol. 24, No. 2, 1994, pp. 145-152.
Database Beilstein, Beilstein Institute for Organic Chemistry, Frankfurt-Main, DE; XP002275030, Database Accession Nos. 3292936, 8911430, 8911858, 8912139, 8912482, (BRN's) & J. Med. Chem., vol. 44, No. 16, 2001, pp. 2544-2554.
Database Beilstein, Beilstein Institute for Organic Chemistry, Frankfurt-Main, DE; XP002275031, Database Accession No. 5535609 (BRN) & Chem. Lett., 1982, pp. 597-600.
Database Beilstein, Beilstein Institute for Organic Chemistry, Frankfurt-Main, DE; XP002275032, Database Accession No. 6727608 (BRN) & Farmaco Ed. Sci., vol. 36, No. 12, 1981, pp. 1037-1056, XP0009028407.
Allegretti, et al, J Med Chem, (2005), vol. 48, pp. 4312-4331.
Barnes, Pharmacological Reviews, vol. 56(4), pp. 515-548.
McCulloch, et al, Nature Reviews Drug Discovery, (2006), vol. 5, pp. 864-876.
Yang, X.D. et al. "Fully human anti-interleukin-8 monoclonal antibodies: potential therapeutics for the treatment of inflammatory disease states." J Leukoc Biol. 1999, 66(3), pp. 401-410.
Schulz, B.S. et al. "Increased expression of epidermal IL-8 receptor in psoriasis. Down-regulation by FK-506 in vitro." J Immunol. 1993, 151(8), pp. 4399-4406.

Kemeny, L., et al. "The interleukin-8 receptor: a potential target for antipsoriatic therapy?" Eur J Pharmacol. 1994, 258(3), pp. 269-272.
Matsumoto, T., et al. "Pivotal role of interleukin-8 in the acute respiratory distress syndrome and cerebral reperfusion injury." J Leukoc Biol. 1997, 62(5), pp. 581-587.
Yokoi, K., et al. "Prevention of endotoxemia-induced acute respiratory distress syndrome-like lung injury in rabbits by a monoclonal antibody to IL-8." Lab Invest. 1997, 76(3), pp. 375-384.
Wallace, J.L., et al. "Reduction of acute and reactivated colitis in rats by an inhibitor of neutrophil activation." Am J Physiol. 1998, 274(5 Pt 1), pp. G802-G808.
Harada, A., et al., "Essential involvement of interleukin-8 (IL-8) in acute inflammation." J Leukoc Biol. 1994, 56(5), pp. 559-564.
Schmidt, E., et al. "The IL-8 release from cultured human keratinocytes, mediated by antibodies to bullous pemphigoid autoantigen 180, is inhibited by dapsone." Clinical & Experimental Immunology. 2001, 124(1), pp. 157-162.
International Search Report for PCT Application No. PCT/EP2003/013946 filed on Dec. 9, 2013 in the name of DOMPE S.P.A. mail date: Apr. 16, 2004.
International Preliminary Examination Report for PCT Application No. PCT/EP2003/013946 filed on Dec. 9, 2013 in the name of DOMPE S.P.A. completion date: Mar. 18, 2005.
Wada, T. et al. "Prevention of Proteinuria by the Administration of Anti-interleukin 8 Antibody in Experimental Acute Immune Complex-induced Glomerulonephritis." Journal of Experimental Medicine. Sep. 1994, vol. 180, pp. 1135-1140.
Seitz, M. et al. "Enhanced Production of Neutrophil-activating Peptide-1/Interleukin-8 in Rheumatoid Arthritis." J. Of Clin. Invest. Feb. 1991, vol. 87, pp. 463-469.
Nickoloff, B.J. et al. "Cellular Localization of Interleukin-8 and its Inducer, Tumor Necrosis Factor-alpha in Psoriasis." American Journal of Pathology, Jan. 1991, vol. 138(1), pp. 129-140.
Carré, P.C. et al. "Increased Expression of the Interleukin-8 Gene by Alveolar Macrophages in Idiopathic Pulmonary Fibrosis." J. Clin. Invest., Dec. 1991, vol. 88, pp. 1802-1810.
Podolin, P.L., et al. "A Potent and Selective Nonpeptide Antagonist of CXCR2 Inhibits Acute and Chronic Models of Arthritis in the Rabbit." Journal of Immunology, 2002, vol. 169, pp. 6435-6444.
Hirani, N. et al. "The Regulation of Interleukin-8 by Hypoxia in Human Macrophages—A Potential Role in the Pathogenesisof the Acute Respiratory Distress." Molecular Medicine, vol. 7(10), 2001, pp. 685-697.
Kulke, R. et al. "The CXC Receptor 2 is Overexpressed in Psoriatic Epidermis." The Society for Investigative Dermatology, vol. 110(1), Jan. 1998, pp. 90-94.
Cole, A.T. et al. "Mucosal factors inducing neutrophil movement in ulcerative colitis: the role of interleukin 8 and leukotriene $B_4$", Gut, 1996, pp. 248-254.
Liu, Z. et al. "A Major Role for Neutrophils in Experimental Bullous Pemphigoid." The Journal of Clinical Investigation, vol. 100(5), Sep. 1997, pp. 1256-1263.
Bizzarri, C. et al. Single-Cell Analysis of Macrophage Chemotactic Protein-1-Regulated Cytosolic $Ca^{2+}$ Increase in Human Adherent Monocytes. Blood. Sep. 1995, vol. 86(6), pp. 2388-2394.
Cather, J. et al., "Novel Therapies for Psoriasis", Am J Clin Dermatol, 2002, 3 (3): 159-173.
Dincan, E. et al., "Electrosynthesis of ketones from organic halides and anhydrides", Tetrahedron Letters, 27 (35), 1986, 4175-4176. Abstract.
European Medicines Agency, Committee for Orphan Medicinal Products, "Public summary of opinion on orphan designation repertaxin L-lysinate salt for the prevention of delayed graft function in organ transplant", EMA/COMP/261/2004 Rev.1. Mar. 10, 2010. 5 pages.
Falk, W. et al., "A 48-well micro chemotaxis assembly for rapid and accurate measurement of leukocyte migration", Journal of Immunological Methods. 1980, vol. 33 (3), 239-247. Abstract.
Folkesson, H.G. et al., "Acid Aspiration-induced Lung Injury in Rabbits is Mediated by Interlukin-8-dependent Mechanisms", J. Clin. Invest., Jul. 1995, vol. 96, 107-116.

(56) References Cited

OTHER PUBLICATIONS

Harris, B.D. et al., "Synthetic studies of didemnins. II. Approaches to statine diastereomers", Tetrahedron Letters. 1987, vol. 28 (25), pp. 2837-2840. Abstract.

Krueger, J.G., "The immunologic basis for the treatment of psoriasis with new biologic agents", J Am Acad Dermatol, Jan. 2002, vol. 46 (1), 1-26.

Lane, B.R. et al., "Interleukin-8 Stimulates Human Immunodeficiency Virus Type 1 Replication and Is a Potential New Target for Antiretroviral Therapy", Journal of Virology, Sep. 2001, vol. 75 (17), 8195-8202.

Matsumoto, T. et al., "Prevention of Cerebral Edema and Infarct in Cerebral Reperfusion Injury by an Antibody to Interleukin-8", Laboratory Investigation, Aug. 1997, vol. 77 (2), 119-123.

Ming, W.J. et al., "Tumor necrosis factor is chemotactic for monocytes and polymorphonuclear leukocytes", Journal of Immunology. 1987, 138 (5), pp. 1469-1474. Abstract.

Mitsuyama, K. et al., "IL-8 as an important chemoattractant for neutrophils in ulcerative colitis and Crohn's disease", Clin Exp Immulog, 1994, 96: 432-436.

Mongelli, N. et al. "1-Fluorocycloalkanecarboxylic Acids in the Synthesis of 16-Achiral 16-Fluoro-9a-carbaprostacyclin Derivatives", Synthesis, 1988 (4), pp. 310-313. Abstract.

Oikawa, Y. et al. "Meldrum's acid in organic synthesis. 2. A general and versatile synthesis of beta-keto esters", Journal of Organic Chemistry, 1978, vol. 43 (10), pp. 2087-2088. Summary.

Takahashi, Y. et al., "The Participation of IL-8 in the Synovial Lesions at an Early Stage of Rheumatoid Arthritis", Tohoku J. Exp. Med., 1999, 188, 75-87.

Wada, T et al., "Prevention of proteinuria by the administration of anti-interleukin 8 antibody in experimental acute immune complex-induced glomerulonephritis", J Exp Med, 1994, 180 (3), 1135-1140. Abstract.

Mahida, Y.R. et al., Enhanced synthesis of neutrophil-activating peptide-1/interleukin-8 in active ulcerative colitis. *Clinical Sci.*, Mar. 1992, vol. 82(3), pp. 273-275.

Liu, J.H. et al., Recombinant Interleukin-8 Induces Changes in Cytosolic $Ca^{2+}$ in Human Neutrophils. *J. Infect. Dis.*, 1992, vol. 166(5), pp. 1089-1096.

Brooks, D.W. et al. C-Acylation under Virtually Neutral Conditions. *Angew. Chem. Int. Ed.* Engl., Jan. 1979, vol. 18(1), pp. 72-74.

Krapcho, J.P., Synthetic Applications of Dealkoxycarbonylations of Malonate Esters, β-Keto Esters, α-Cyano Esters and Related Compounds in Dipolar Aprotic Media—Part I. Synthesis, 1982, (10), pp. 805-822.

Krapcho, J.P., Synthetic Applications of Dealkoxycarbonylations of Malonate Esters, β-Keto Esters, α-Cyano Esters and Related Compounds in Dipolar Aprotic Media—Part II. Synthesis, 1982, (11), pp. 893-914.

Houghton, R.P. et al., A Modified Preparation of β-Keto Esters. *Synthesis.* 1982, (6), pp. 451-452.

Chan, C.C. et al., Synthesis of Isopropylidene Dialkylmalonates under Phase-Transfer Catalyzed Conditions, *Synthesis*, (1982), (6), pp. 452-454.

Malevannaya, R.A. et al., (Dialkoxyphosphinyl)Acetic Acids and some of their Analogs, in Zh. Obshch. Khim. 41, 1426 (1971), *J. Gen. Chem.* USSR (Engl. Transl.), 41, pp. 1432-1439, 1971.

Miller, E.J. et al., Elevated Levels of NAP1/Interleukin-8 Are Present in the Airspaces of Patients with the Adult Respiratory Distress Syndrome and Are Associated with Increased Mortality, *Am. Rev. Respir. Dis.*, 146(2), pp. 427-432, 1992.

D'Incan, E. et al., Electrosynthesis of Ketones From Organic Halides and Anhydrides, *Tetr. Lett.* 27, No. 35, pp. 4175-4176, 1986.

Mongeili, N. et al. 1-Fluorocycloalkanecarboxylic Acids in the Synthesis of 16-Achiral 16-Fluoro-9a-carbaprostacyclin Derivatives. *Synthesis.* 1988, (4), pp. 310-313.

Harris, B.D. et al., Synthetic studies of didemnins. II. Approaches to statine diastereomers. *Tetrahedron Letters.* 1987, vol. 28 (25), pp. 2837-2840.

Oikawa, Y. et al., Meldrum's acid in organic synthesis. 2. A general and versatile synthesis of beta.-keto esters. *Journal of Organic Chemistry.* 1978, vol. 43 (10), pp. 2087-2088.

Ming, W.J. et al., Tumor necrosis factor is chemotactic for monocytes and polymorphonuclear leukocytes. *Journal of Immunology.* 1987, vol. 138, No. 5, pp. 1469-1474.

Falk, W. et al., A 48-Well Micro Chemotaxis Assembly for Rapid and Accurate Measurement of Leukocyte Migration, Journal of *Immunological Methods.* 1980, vol. 33 (3), pp. 239-247.

Wada, T. et al., Prevention of proteinuria by the administration of anti-interleukin 8 antibody in experimental acute immune complex-induced glomerulonephritis, *J Exp Med*, 1994, 180 (3), pp. 1135-1140.

\* cited by examiner

CHIRAL ARYLKETONES IN THE TREATMENT OF NEUTROPHIL-DEPENDENT INFLAMMATORY DISEASES

This application is a Continuation of copending U.S. application Ser. No. 10/537,824, filed on Feb. 8, 2006, which is a National Stage of PCT International Application No. PCT/EP03/13946 filed on Feb. 8, 2006, which designated the United States, and on which priority is claimed under 35 U.S.C. §120. This application also claims priority under 35 U.S.C. §119(a) on Patent Application No(s). EP 02027453.6 filed in Italy on Dec. 10, 2002. The entire contents of each of the above documents is hereby incorporated by reference.

The present invention relates to chiral arylketones, a process for their preparation, and pharmaceutical compositions containing them, which are useful in the prevention and treatment of tissue damage due to the exacerbated recruitment of polymorphonucleate neutrophils in the inflammatory sites.

Other classes of compounds, such as R-2-arylpropionic acid amides and N-acylsulfonamides useful in the prevention and treatment of tissue damage due to the exacerbated recruitment of polymorphonucleate neutrophils in the inflammatory sites, have been described in WO 01/58852 and WO 00/24710 respectively. The compounds of the invention are generally known compounds and disclosed in Belstein Handbook of Organic Chemistry.

DETAILED DESCRIPTION OF THE INVENTION

More specifically, the present invention relates to chiral arylketones of general formula I:

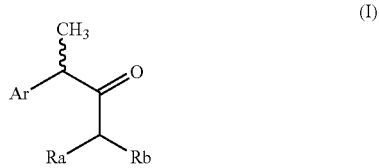

wherein:
Ar is an aryl group;
Ra and Rb are independently chosen in the group of hydrogen, linear or branched $C_1$-$C_6$ alkyl, phenyl, α- or β-naphthyl, 2,3,4-pyridyl, $C_1$-$C_4$-alkylphenyl, $C_1$-$C_4$-alkyl α- or β-naphthyl), $C_1$-$C_4$-alkyl(2,3,4-pyridyl), cyano (—CN), carboxyamide, carboxyl or carboxyesters of formula $CO_2R''$ wherein R'' is the residue of a linear or branched $C_1$-$C_6$ aliphatic alcohol, a phosphonate $PO(OR'')_2$ wherein R'' is as defined above, a group of formula di-X—$(CH2)_n$-Z, wherein X is a CO, SO, $SO_2$ group; Z is H; tert-butyl, isopropyl, $CO_2R''$, CN, phenyl, α- or β-naphthyl, 2,3,4-pyridyl, $C_3$-$C_6$ cycloalkyl, NH—BOC, $NH_2$; n is zero or an integer from 1 to 3; or Ra and Rb, with the carbon atom to which they are bound, form a cyclic residue 4,6-dioxo-1,3-dioxanyl-2,2-disubstituted of formula II:

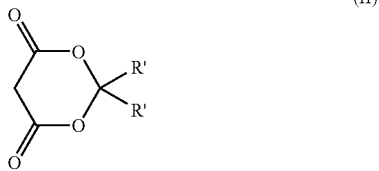

wherein R' is methyl or ethyl, or the two groups R' form a cyclohexane or cyclopentane ring.

By aryl group is meant preferably phenyl, optionally substituted by one to three substituents, which are the same or different from one another, selected from atoms of halogen, $C_1$-$C_4$-alkyl, $C_1$-$C_4$-alkoxy, hydroxy, $C_1$-$C_4$-acyloxy, phenoxy, cyano, nitro, amino, $C_1$-$C_4$-acylamino, halogen-$C_1$-$C_3$-alkyl, halogen $C_1$-$C_3$-alkoxy, benzoyl, or the aryl portion of known anti-inflammatory 2-aryl-propionic acids, such as ibuprofen, ketoprofen, naproxen, surprofen, carprofen, pirprofen, and fenoprofen.

Preferred residues of 2-aryl-propionic acid are: 4-iso-butyl-phenyl, 3-benzoylphenyl, 5-benzoyl-2-acetoxy-phenyl, 3-phenoxy-phenyl, 5-benzoyl-2-thiophenyl, 4-thienoyl-phenyl, 1-oxo-2-isoindolinyl-phenyl, 3-chloro-4-(2,5-dihydro-1H-pyrrol-1-yl)phenyl, 6-methoxy-β-naphthyl, 1-hydroxy-phenyl-1-methyl, or a residue of formula III:

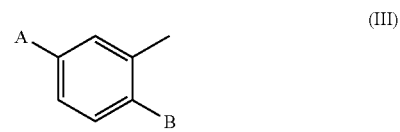

wherein A is benzyl, phenoxy, benzoyl, benzoyloxime, 1-hydroxy-phenyl-1-methyl, B is hydroxy, C1-C4-acyloxy, or a group of formula —O—C(═S)—N(CH3)2; —S—C(═O)—N(CH3)2. R is preferably an aryl residue of a known anti-inflammatory 2-aryl-propionic acid, as defined above; more preferably, R represents: 4-(2-methyl-propyl)-phenyl, 3-phenoxy-phenyl, 3-benzoylphenyl, 2-[4-(1-oxo-2-isoindolinyl)phenyl], 5-benzoyl-thien-2-yl, 4-thienoyl-phenyl.

Preferred linear or branched $C_1$-$C_6$ alkyl and of a residue of $C_1$-$C_6$ aliphatic alcohol are methyl and ethyl; $C_1$-$C_4$ alkyl is preferably isobutyl; $C_1$-$C_4$-acyloxy is preferably acetyloxy.

Particularly preferred compounds of formula I of the invention are those compounds wherein the steric configuration of the carbon atom to which the residue R is bound corresponds to the configuration (R).

The following compounds:

(R,S) (±)-2-butanone, 3-[4-(2-methylpropyl)phenyl] (CAS no-64758-90-3);

(R,S) (±)-2-butanone, 3-(3-phenoxyphenyl) (CAS no108671-27-8);

(R,S) (±)-2-butanone, 3-(3-benzoylphenyl) (CAS no79868-87-4);

ethyl (R,S) (±)-4-(3-benzoyl-phenyl)-3-oxo-pentanoate (CAS no145927-45-3);

(R,S) (±)-1; 3-dioxan-4,6-dione-, 5-[2-(3-benzoylphenyl-1-oxopropyl)]-2,2-dimethyl (CAS no154 023-15-1);

are known as racemic intermediates for the preparation of 2-arylpropionic acids [JP 03024023 (2 Jan. 1991); JP 52108949 (9 Dec. 1991); JP 52083426 (7 Jan. 1977); JP 56097249 (8 May 1981); Tetr. Lett. 27. 4175, 1986] and of thiazoles [EP 511021; (28 Oct. 1992); JP 0528902 (11 Feb. 1993)].

The compounds of formula (I) are obtained by reacting an activated 2-arylpropionic acid of formula IV:

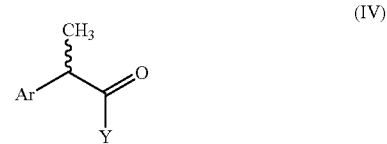

wherein
Ar is as above defined aryl and Y is a residue activating the carbonyl, preferably a halogen, such as chlorine, 1-imida zolyl, pivaloyl, $C_1$-$C_3$-alkoxycarbonyl, succinyloxy, benzotriazol-1-yloxy

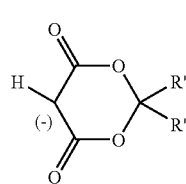

(Va)

with a carbanion of formula V:

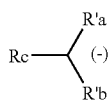

(V)

wherein:
when R'a is the residue of a complex between a carboxyl and magnesium ethoxide, R'b is $CO_2R''$, $CONH_2$, CN, $PO(OR'')_2$ or —X—$(CH_2)$n-Z', where X is as defined previously; Rc is H or —$(CH_2)_n$—Z', where Z' is H, tert-butyl, isopropyl, $CO_2R''$, CN, phenyl, α- or [β-naphthyl, 2,3,4-pyridyl, $C_3$-$C_6$ cycloalkyl, NH—BOC;

when R'a is hydrogen and Rc is hydrogen or a —$(CH_2)_n$—Z' radical, as defined above, R'b is phosphonate $PO(OR'')_2$, $CO_2R''$, or R'a and R'b with the carbon atom to which they are bound, form the carbanion at the carbon atom $C_5$ of a radical 2,4-dioxo-1,3-dioxanyl of formula Va:

wherein R' has the meanings indicated above, to yield a compound of formula (Ia):

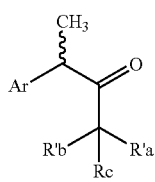

(Ia)

wherein R'a, R'b and R'c have the meanings described above, provided that Rc is hydrogen when R'a and R'b with the carbon atom to which they are bound form 4,6-dioxo-1,3-dioxanyl of formula (II), also known as Meldrum adduct of formula Ib:

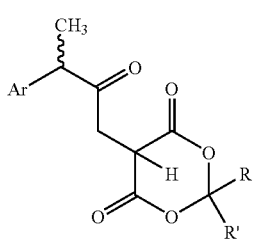

(Ib)

wherein Ar and R' have the meanings described above. If so desired, the Meldrum adducts are converted by boiling in a linear or branched $C_1$-$C_6$ alcohol into the corresponding β-ketoester of formula Ic:

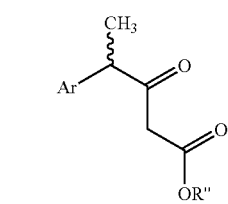

(Ic)

A β-ketoester of formula Ia and Ic may optionally be dealkoxydecarboxylated to the corresponding arylketone of formula I by simply heating in an aprotic solvent (preferably dimethylsulfoxide) in the presence of small amounts of water and, optionally, of small amounts of electrolytes, such as NaCl, NaCN, LiCl, LiI (according to J. P. Krapcho, Synthesis 805 and 893, 1982, and references cited herein). Likewise, using well known methods, a compound of formula Ia can be converted into another compound of formula I by removal of any protective groups that may be present, or by saponification of carboxyl groups, or by conversion of nitrites into carboxyamides.

The compounds of formula IV are obtained in a conventional way, conserving their enantiomeric integrity, starting from the individual enantiomers of the 2-aryl-propionic acids of formula IVa:

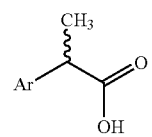

(IVa)

which are known compounds and can be obtained from the individual racemates using known methods of optical resolution.

The preparation of the carbanions of formula V consists in a process of C-acylation in virtually neutral conditions; fully described in the literature (see, for example, D. W. Brooks et al., Angew. Chem. Int. Ed. Engl., 18, 72, 1979), as well as monoesters of malonic acids and of monosubstituted malonic acids, also on sulfinylacetic acids, sulfonylacetic acids and phosphonoacetic acids. All these acids are known in the literature or can be prepared using known methods, such as monosaponification of diesters of malonic acids and their monosubstituted analogues or saponification of phosphonoacetic acids and 2-substituted analogues; sulfinylacetic and sulfonylacetic acids may be obtained by oxidation of ethers of thioglycolic acid. Alternatively, it is possible to use lithium enolates of formula V, obtained by reaction of lithium alkyls with known alkyl esters of alkylphosphonates (see, for example, N. Mongeili et al., Synthesis, 310, 1988) or with esters of acetic acid (according to D. H. Harris et al., Tetrah. Lett., 28, 2837, 1987).

For the preparation of enolates of formula Va, and more generally for the procedure of acylation of the cyclic alkylidenesters of malonic acid (also known as Meldrum acids) with the activated species of a carboxyl of formula IV, the method described by Y. Oikawa et al., J. Org. Chem., 43, 2087 (1978), R. P. Houghton and D. J. Lapham, Synthesis 451 (1982) and C. C. Chan and X. Hung, ibidem, 452 (1982) is used.

The preparation of dialkoxyphosphonoacetic acids and that of their esters are exemplified in U.S. Pat. No. 4,151,172 (Apr. 24, 1979), or described by R. A. Malevannaya et al., in Zh. Obshch. Khim. 41, 1426 (1971).

Specific examples of the compounds of the invention are:
methyl (R)(−)-4-[(4'-isobutyl)phenyl]-3-oxopentanoate;
methyl (S)(+)-4-[(4'-isobutyl)phenyl]-3-oxopentanoate;
(R,S) 4-[(4'-isobutyl)phenyl]-3-oxopentanoic acid;
methyl (R)(−)-4-[(3'-benzoyl)phenyl]-3-oxopentanoate;
(R)(−)-3-[(4'-isobutyl)phenyl]butan-2-one;
(S)(+)-3-[(4'-isobutyl)phenyl]butan-2-one;
(R)(−)-3-[(3'-benzoyl)phenyl]butan-2-one;
(R)(−)-dimethyl 3-(4-isobutyl)-2-oxobutan-1-phosphonate;
(S)(±)-dimethyl 3-(3'-phenoxy-phenyl)-2-oxo-butyl-1-phosphonate;
(R)(−)-2-(4-isobutylphenyl)-pentan-3-one;
(S)(+) ethyl-4-[(3'-benzoyl)phenyl]-3-oxopentanoate;
(S)(+)-3-[(3'-benzoyl)phenyl]butan-2-one;
(R)(−)-2-(4-isobutylphenyl)-4-phenyl-butan-3-one;
(R)(−)-2-(4-isobutylphenyl)-5-phenyl-pentan-3-one;
(R)(−)-2-(4-isobutylphenyl)-5-(pyrid-3-yl)-pentan-3-one;
(R)(−) methyl 4-[(4'-benzoyloxy)phenyl]-3-oxopentanoate;
(R)(−) methyl-4-[(4'-isopropylsulfonyloxy)phenyl]-3-oxopentanoate;
(R)(−) methyl-4-{[4'-(2"-ethyl)phenylsulfonylamino]phenyl}-3-oxopentanoate;
(R,S) 5-(4'-isobutylphenyl)-hexan-2,4-dione;
(R,S)1-phenyl-5-(4'-isobutylphenyl)-2,4-hexandione;
(R,S) 1-(pyrid-2-yl)-4-(4'-isobutylphenyl)-1,3-pentadione;
(R) (−) 2-(4-isobutylphenyl)-7-tert-butoxycarbonylamino-heptan-3-one;
(R,S) 2-(4'-isobutylphenyl)-3-oxo-butyl, methyl-sulfoxide;
(R,S) 2-(3'-benzoylphenyl)-3-oxo-butyl, methyl-sulfoxide;
(R,S) 2-(4'-isobutylphenyl)-3-oxo-butyl, methyl-sulfone;
(R,S) 2-(3'-benzoylphenyl)-3-oxo-butyl, methyl-sulfone;
(R,S) 2-(3'-phenoxyphenyl)-3-oxo-butyl, methyl-sulfone;
(R,S) 2-(4'-isobutylphenyl)-3-oxo-butyl, phenyl-sulfone;
(R)(−)-4-(4'-pyridyl)-2-[(4"-isobutyl)phenyl]butan-3-one;
(R)-2-[4-(1-oxo-2-isoindolinyl)phenyl]-3-oxo-valeramide;
(R)-2-[4-(1-oxo-2-isoindolinyl)phenyl]-3-oxo-valeronitrile;
(R) (+) 5-[2-(4-isobutyl-phenyl)-propion-1-yl]-2,2-dimethyl-1,3-dioxan-4,6-dione;
(R) (−)-5-[2-(3'-benzoyl-phenyl)-propion-1-yl]-2,2-dimethyl-1,3-dioxan-4,6-dione;

The compounds of formula I are powerful inhibitors of the chemiotaxis of the neutrophils induced by IL-8 and inhibit the amplification of the production of TNF-α stimulated by lipopolysaccharides and by hydrogen peroxide. An exacerbated production of hydrogen peroxide is notoriously the final consequence of the neutrophilic activation consequent upon a chemiotactic stimulus.

Examples of β-ketoesters of formula I are methyl R(−)-4-[(4'-isobutyl)phenyl]-3-oxopentanoate and methyl R(−)-4-[(3'-benzoyl)phenyl]-3-oxopentanoate, which, at the concentration of $10^{-8}$ M, inhibit the chemiotaxis of human neutrophils to an extent higher than 50% as compared to control values.

A typical example of 2-aryl-alkan-3-one is R(−)-3-[(4'-isobutyl)phenyl]butan-2-one for which an $IC_{50}$ of $5.10^{-10}$ M has been calculated in the same in vitro inhibition assay.

For evaluation of the compounds of the invention, polymorphonucleated blood cells were used obtained from heparinized blood of healthy adult volunteers by means of sedimentation on dextran. The mononucleated cells were removed by means of Ficoll/Hypaque, whilst the red blood cells were eliminated by treatment with hypotonic solutions. The cell vitality of the polymorphonucleated leucocytes (PMNs) was calculated by means of exclusion with Turk and Trypan Blue whilst after staining with Diff Quinck the percentage of the PM-nucleates on the cytocentrifugate was estimated (for details of the experimental techniques used see W. J. Ming et al., J. Immunol., 138, 1469, 1987). In each of the in vitro experiments, time periods of 10 minutes were used for the incubation of the PMNs with the compounds of the invention, operating at a temperature of 37° C.

In the experiments of chemiotaxis and in those designed for measuring the cytosol levels of the $Ca^{2+}$ ion, human recombinant IL-8 (Pepro Tech.) was used as stimulant: the liophilized protein was dissolved in HBSS (Hank's balanced salts solution) at a concentration of 100 ng/mL and was used after dilution in HBSS down to concentrations of 10 ng/mL in the chemiotaxis experiments and at the concentration of 25-50 ng/mL in the evaluation of the modifications of $[Ca^{2+}]$.

In the chemiotaxis assay (according to W. Faiket et al., J. Immunol. Methods, 33, 239, 1980) PVP filters were used having a porosity of 5 µm and a Plexiglas microchamber suitable for making 48 replications. The microchamber consists of a block of Plexiglas containing 48 wells, each having a capacity of 25 µL and is provided with a lid, which in turn contains 48 pores arranged in such a way that, once the lid has been set in place and screwed to the underlying part, it comes to form the top compartments of the microchamber, each having a capacity of 50 µL.

The compounds under study were added at one and the same concentration in the wells of higher level, which contain the suspension of PMNs and in the wells of lower level, which contain the vehicle to which IL-8 (or a different stimulant) has been added or not.

For determination of the cytosol variations of the $[Ca^{2+}]_i$, the experimental model described by C. Bizzarri et al., (Blood, 86, 2388, 1995) was adopted, using slides containing adhered PMNs, which were fed with 1 µM of Fura-2AM in order to evaluate said variations of $[Ca^{2+}]_i$ in real time. In turn, cytocentrifugates of PMNs were resuspended in RPMI medium 1640 with 5% of FCS (foetal cow serum) at a concentration of $3\times10^6$/mL and then plated on round glass slides of a diameter of 25 mm, which were placed in an incubator for 30 min at 37° C. After three consecutive washings with balanced salts solution (BSS) to remove the non-adherent cells, a further incubation was performed for the set of adherent cells for a maximum of 4 hours before feeding with Fura-2AM.

The compounds of the invention prevent the increase in the intracellular concentration of $Ca^{2+}$ induced by IL-8.

The compounds of the invention are characterized by their capacity for inhibiting in vitro the chemiotaxis of the human PMN leucocytes (PMNs) stimulated by interleukin 8, also known as "monocyte-derived neutrophil-activating: protein" (NAP/IL-8 or more simply IL-8). Said inhibition is dose-dependent, with values of $IC_{50}$ (dose inhibiting 50% of the effect) in the $0.10^{-7}$ to $10^{-9}$-M range; the inhibiting effect is selective and specific in regard to the chemiotactic stimulus induced by IL-8. Concentrations higher by one or two orders of magnitude are needed to inhibit the chemiotaxis stimulated in vitro by other chemiotactic factors (C5a, formylpeptides of bacterial origin or synthetic origin, such as f-LMP). The specificity of the compounds of the invention is moreover demonstrated by their capacity to inhibit the increase in the intracellular concentration $[Ca^{2+}]_i$ in human PMNs, an increase that is associated to the activation of the human PMNs themselves by IL-8 [J. H. Liu et al., J. Infect. Dis., 166, 1089 (1992)].

Independently of the absolute configuration, the compounds of the invention are without significant effects on cyclooxygenasis and on the production of PG.

In fact, in murine macrophages stimulated by LPS (1 μg/mL), the compounds of the invention (evaluated in the range of concentration of $10^{-5}$ to $10^{-7}$ M) show an inhibition of the production of $PGE_2$ which, albeit frequently at the limit of statistical significance, is never higher than 10 to 15% of the basal value.

The above minor inhibition of the synthesis of $PGE_2$ involves the advantage, unlike what occurs for certain 2-arylpropionic acids, of not constituting a stimulus that is likely to amplify the synthesis of TNF-α by the murine macrophages themselves (once they have been stimulated by LPS). The amplification of the synthesis of TNF-α is considered to concur, in turn, in amplifying the activation and chemiotaxis of the neutrophils and the synthesis of IL-8. On the other hand, these effects of non-amplification of the synthesis of TNF-α are shown also in regard to the synthesis of TNF-α stimulated by hydrogen peroxide.

It is known that interleukin 8 (IL-8) and the correlated cytokines are the most important modulators of the infiltration of the neutrophils in diseases such as psoriasis (B. J. Nickoloff et al., Am. J. Pathol., 138, 129, 1991), rheumatoid arthritis (M. Selz Seitz et al., J. Clin. Invest. 87, 463, 1991), ulcerative cholitis (Y. R. Mahkla Mahida et al., Clin. Sci., 82, 273, 1992), acute respiratory distress syndrome (ARDS), idiopathic fibrosis (P. C. Carré et al., J. Clin. Invest., 88, 1802, 1991 and E. J. Miller et al., Am. Rev. Respir. Dis., cited above), glomerulonephritis (T. Wada et al., J. Exp. Med., 180, 1135, 1994) and bollous pemphigo.

The compounds of the invention are then used for the treatment of said diseases, conveniently formulated in pharmaceutical compositions using conventional techniques and excipients.

The compounds of the invention are also conveniently used for the prevention and the treatment of damages caused by ischemia and reperfusion; in particular in connection with organ transplantation.

The compositions of the invention can be administered via intramuscular injection; via intravenous route, as a bolus, in preparations for dermatological use (creams, lotions, sprays and ointments), as well as via oral route in the form of capsules, tablets, syrup, controlled-release formulations, and the like.

The mean daily dosage will depend upon various factors, such as the severity of the illness and the conditions of the patient (age, sex and weight). The dose will vary generally from one mg or a few mg up to 1500 mg of the compounds per day, optionally divided into multiple administrations. Higher dosages, as well as more prolonged treatment times, can be administered also by virtue of the low toxicity of the compounds of the invention.

The following examples are provided by way of illustration of the invention. The examples are not construed to be viewed as limiting the scope of the invention.

Example 1

(R)(−)-3-[(4'-isobutyl)phenyl]butan-2-one (R) (−)-ibuprofen (2 g, 9.69 mmol) is dissolved in thionyl chloride (4 mL), and the solution obtained is refluxed for 4 hours.

After cooling to room temperature, the solvent is evaporated at reduced pressure, and the excess of thionyl chloride is eliminated by dissolving the residue twice with dioxane and evaporating the solvents at a high vacuum. The oily yellow residue (2.34 g; 9.34 mmol) thus obtained, is dissolved in dry dichloromethane (3 mL) and added, by means of slow dripping and in an inert-gas atmosphere, to a solution of 2,2-dimethyl-1,3-dioxan-2,5-dione (Meldrum's acid) (1.35 g; 9.34 mmol) and pyridine (1.83 mL; 22.9 mmol) in dry dichloromethane (7.5 mL) previously cooled to 0-5° C. with a water/ice bath. Once the additions are completed, the product is left for one hour at this temperature and then for another hour at room temperature. The mixture diluted with dichloromethane is partitioned with a 2N HCl and crushed ice, under vigorous stirring for 30 min. After separation of the phases, the organic phase, washed with 2N HCl (2×10 mL) and with a saturated solution of NaCl, is dried on $Na_2SO_4$. After evaporation of the solvents at reduced pressure, 2.69 g of R(+)-5-[2-(4-isobutyl-phenyl)-propion-1-yl]-2,2-dimethyl-1,3-dioxan-4,6-dione is obtained as an oil. ($[\alpha_D]$=+61.7°; c=1% $CH_2Cl_2$) which, without further purifications, is dissolved in dioxane (10 mL). Glacial acetic acid (0.84 mL) and water (0.13 mL) are added; and the resulting solution is heated to the reflux temperature for 3 hours. After cooling and evaporation of the solvents, the residue is purified by means of flash chromatography (eluent: n-hexane/ethyl ether 9:1) to yield (R) (−)-3-[(4'-isobutyl)phenyl]butan-2-one as a pale yellow oil (0.97 g; 475 mmol). $[\alpha]_D$=−216.1° (c=1; $CH_3CH_2OH$); $^1$H-NMR ($CDCl_3$): σ 6.95 (s, 4H); 3.61 (q, 1H, J=8 Hz); 2.3 (d, 3H, J=7 Hz); 1.93 (s, 3H); 1.75 (m, 1H); 1.26 (d, 2H, J=8 Hz); 0.85 (d, 6H, 7=7 Hz).

Example 2

(S) (+)-3-[(4'-isobutyl)phenyl]butan-2-one (R) (−)-3-[(3'-benzoyl)phenyl]butan-2-one Following the procedure of Example 1, using 0.3 g (1.33 mmol) of S (+)-ibuprofen S(+)-3-[(4'-isobutyl)phenyl]butan-2-one is obtained (0.13 g, 0.63 mmol) as a pale yellow oil; $[\alpha]_D$=+210.5 (c=1; $CH_3CH_2OH$); $^1$H-NMR ($CDCl_3$); σ 7.10 (s, 4H); 3.75 (q, 1H, J=8 Hz); 2.45 (d, 3H, J=7 Hz); 2.05 (s, 3H); 1.85 (m, 1H); 1.32 (d, 2H, J=8 Hz); 0.92 (d 6H, J=7 Hz). Likewise, starting from 0.74 g (2.9 mmol) of (R) (−)-ketoprofen, 0.46 g (179 mmol) of R(−)-3-[(3'-benzoyl)phenyl]butan-2-one are obtained as a yellow oil $[\alpha]_D$=103° (C=1; $CH_3OH$); $^1$H-NMR ($CDCl_3$): σ 7.85 (m, 2H); 7.75 (m, 2H); 7.60 (m, 1H); 7.55-7.40 (m, 4H); 3.85 (q, 1H, J=8 Hz); 2.1 (s, 3H); 1.45 (d, 3H, J=8 Hz).

Example 3 methyl (R)(−)-4-[(4'-isobutyl)phenyl]-3-oxopentanoate

4-[(4'-isobutyl)phenyl]-3-oxopentanoic Acid (R) (−)-ibuprofen (1.2 g, 5.8 mmol) is dissolved in dioxane (5 mL); thionyl chloride (2.36 mL) is added and the solution obtained is refluxed and left to reflux for 3 hours. After cooling to room temperature, the solvent is evaporated at reduced pressure, and the excess of thionyl chloride is eliminated, dissolving the residue twice with dioxane and evaporating the solvents under high vacuum. An oily yellow residue (1.3 g; 5.79 mmol) is obtained, which is dissolved in dry dichloromethane (2 mL) and added, by means of slow dripping and in an inert atmosphere, to a solution of 2,2-dimethyl-1,3-dioxan-2,5-dione (Meldrum's acid) (0.83 g; 5.79 mmol) and pyridine (1.12 mL; 14 mmol) in dry dichloromethane (5 mL)

previously cooled to T=+5° C. with a water/ice bath. Once the additions are completed, the mixture is left for one hour at this temperature and then for another hour at room temperature. The mixture, diluted with dichloromethane is repartitioned with a 2N solution of HCl and crushed ice, under vigorous stirring for approximately 30 min. After separation of the phases, the organic phase, washed with 2N HCl (2×10 mL) and with a saturated solution of NaCl, is dried on $Na_2SO_4$ after evaporation of the solvent at reduced pressure, the residue of (R) (+)-5-[2-(4-isobutyl-phenyl)-propion-1-yl]-2,2-dimethyl-1,3-dioxan-4,6-dione ($[\alpha]_D$=+62°; c=1.1% $CH_2Cl_2$) without further purifications, is dissolved in methanol (14 mL); the solution is reheated to reflux for 3 hours. After cooling and evaporation of the solvent, the residue is purified by means of flash chromatography (eluent: n-hexane/ethyl ether 8:2) to yield pure methyl ester of (R) (−)-4-[(4'-isobutyl)phenyl]-3-oxopentanoic acid as a colourless oil (0.6 g; 2.28 mmol); $[\alpha]_D$=−192.5° (c=1; $CH_3OH$); $^1$H-NMR ($CDCl_3$): σ 7.1 (s, 4H); 3.88 (q, 1H, J=8 Hz); 3.67 (s, 3H); 3.47-3.28 (q, 2H, J=8 Hz); 2.45 (d, 2H, J=8 Hz); 1.85 (m, 1H); 1.40 (d, 3H, J=8 Hz); 0.95 (d, 6H, J=7 Hz).

To a solution in methanol (2 mL) of 0.15 g (0.57 mmol) of said ester is added a solution of 1N NaOH (1 mL); and the mixture is stirred at room temperature overnight. The solvents are then evaporated at reduced pressure; the residue is dissolved with water (3 mL), and 2N HCl is added by dripping up to pH=1 the mixture is then extracted with ethyl ether (3×10 mL); the organic phase is then washed with a saturated solution of NaCl (10 mL), dried on $Na_2SO_4$, and evaporated at reduced pressure to yield 0.12 g (0.48 mmol) of pure (+) 4-[(4'-isobutyl)phenyl]-3-oxopentanoic acid, as a colourless oil;
$^1$H-NMR ($CDCl_3$): σ 7.1 (m 4H); 3.88 (q, 1H, J=8 Hz); 3.45 (m, 2H); 2.48 (d, 2H, J=8 Hz); 1.90 (m, 1H); 1.45 (d, 3H, J=8 Hz); 0.90 (d, 6H, J=7 Hz).

Example 4 methyl (R) (−)-4-[(3'-benzoyl)phenyl]-3-oxopentanoate

By substituting the R-ibuprofen with 0.74 g (2.9 mmol) of R(−)-ketoprofen in the process of Example 3, 0.81 g of (R) (−)-5-[2-(3'-benzoyl-phenyl)-propion-1-yl]-2,2-dimethyl-1,3-dioxan-4,6-dione are obtained ($[\alpha]_D$=−39.5°; c=1% $CH_2Cl_2$), which, by boiling in methanol yields, after purification by flash chromatography (eluent: n-hexane/ethyl acetate 8:2), 0.49 g (1.56 mmol) of pure methyl (R) (−)-4-[(3'-benzoyl)phenyl]-3 oxopentanoate as a colourless oil, $[\alpha]_D$=135° (c=1; $CH_3OH$); H NMR. ($CDCl_3$): σ 7.85-7.40 (m, 9H); 4.0 (q, 1H, J=8 Hz); 3.70 (s, 3H); 3.50-3.30 (q, 2H, J=8 Hz); 1.45 (d, 3H, J=8 Hz).

Example 5

(S) (+) ethyl-4-[(3'-benzoyl)phenyl]-3-oxopentanoate (S) (+)-3-[(3'-benzoyl)phenyl]butan-2-one At room temperature, in an inert-gas atmosphere and under stirring, to a suspension of magnesium ethylate (0.57 g) in 6 mL of anhydrous THF a solution of mono-ethylester malonic acid (1.3 g) in 3 mL of THF is added. After complete solution of the reagents, to the mixture of the complex magnesium-malonic ethylester, by rapid dripping, a solution of S(+) 2-(3-benzoylphenyl) propionylimidazolide (0.83 g) in 10 mL of anhydrous THF is added, prepared in situ by addition of 0.43 g of 1,1'-carbonyldiimidazole to a solution of S(+) 2-(3-benzoylphenyl) propionic acid (0.66 g) in THF. The mixture is stirred for 4 hours, then is acidified by addition of 50% aqueous AcOH (1.2 mL) and is concentrated under vacuum at a small volume and diluted with water. After repeated extractions with ethyl acetate, the organic phases are combined, rinsed with a saturated solution of NaCl, dried on sodium sulfate, and evaporated to dryness to yield, after purification on silica gel, 0.82 g of ethyl (S) (+)-4-[(3'-benzoyl)phenyl]-3-oxopentanoate;
$[\alpha]_D$=+129° (c=1; $CH_3OH$) $^1$H-NMR ($CDCl_3$): σ 7.82-7.45 (m, 9H); 4.1 (q, 1H, J=8 Hz); 3.75 (s, 3H); 3.50-3.25 (q, 2H, J=8 Hz); 1.48 (d, 3H, J=8 Hz)

According the same described procedure and starting from the corresponding arylpropionic acids the following 3-oxoesters have been synthesised:

(R)(−) methyl 4-[(4'-benzoyloxy)phenyl]-3-oxopentanoate $^1$H-NMR ($CDCl_3$): σ 8.02 (m, 2H); 7.51 (m, 1H); 7.35 (m, 2H); 7.27 (s, 1H); 7.22 (m, 2H); 3.85 (m, 2H); 3.74 (s, 3H); 3.42-3.37 (q, 2H, J=8 Hz); 2.78 (q, 2H, J=8 Hz); L25 (t, 3H, J=8 Hz).

(R)(−) methyl-4-[(4'-isopropylsulfonyloxy)phenyl]-3-oxopentanoate $[\alpha]_D$=−184.2° (c=1; $CH_3OH$); $^1$H-NMR ($CDCl_3$): σ 7.32 (d, 2H, J=7 Hz); 7.21 (d; 2H, J=7 Hz); 4.1 (q, 1H, J=8 Hz); 3.81 (m, 1H); 3.70 (s, 3H); 3.50-3.30 (q, 2H, J=8 Hz); 1.75 (d, 6H, J=7 Hz); 1.45 (d, 3H, J=8 Hz).

(R)(−) methyl-4-{[4'-(2"-ethyl)phenylsulfonylamino]phenyl}-3-oxopentanoate $[\alpha]_D$=−81.3° (c=1; $CH_3OH$); $^1$H-NMR ($CDCl_3$): σ 7.32 (d, 2H, J=7 Hz); 7.20 (m, 6H); 6.84 (bs, 1H, SO2NH); 4.05 (q, 1H; J=8 Hz); 3.72 (s, 3H); 3.55-3.35 (q, 2H, J=8 Hz); 2.75 (q, 2H, J=8 Hz); 1.45 (d, 3H, J=8 Hz); 1.22 (t, 3H, J=8 Hz). A solution of 0.4 g of the compound in 1.5 mL of dimethylsulfoxide, to which 2 drops of a saturated aqueous solution of NaCl are added, is heated for 4 hours, under stirring, in a bath at 140-145° C.; after cooling and dilution with water, the mixture is extracted repeatedly with ethyl acetate. From the combined organic phases, after the usual processing, an oily residue is obtained which, after purification by flash chromatography, yields 0.24 g of S (+)-3-[(3'-benzoyl)phenyl]butan-2-one as a yellow oil; $[\alpha]_D$=+101° (c=1; $CH_3OH$); $^1$H-NMR ($CDCl_3$) σ 7.83 (m, 2H); 7.77 (m, 2H); 7.65 m, 1H); 7.50-7.45 (m, 4H); 3.85 (q, 1H, J=8 Hz); 2.3 (s; 3H); 1.40 (d, 3H, J=8 Hz).

Example 6

(R.) (−)-dimethyl 3-(4-isobutylphenyl)-2-oxobutan-1-phosphonate

A solution of (R) (−)-ibuprofen (3.45 g) in ethyl ether, cooled to 5° C., is treated, dropwise, with a 0.6 M solution of diazomethane in ethyl ether, up to a persistent yellow colour. The solvent is removed—under vacuum; the residual oil is purified by flash chromatography to yield 3.3 g of methyl (R) (−) 2-(4'-isobutylphenyl)-propionate.

Alternatively, 2.6 g of carbonyldiimidazole are added under stirring to a solution of R(−) Ibuprofen (3.45 g) in 10 mL of THF. The mixture is stirred for 1 h, the solvent is evaporated under vacuum; and the residual oil is purified by flash chromatography to yield 4.05 g of (R) (−) 2-(4'-isobutylphenyl)-propionylimidazolide.

In an inert-gas atmosphere, a solution of butyl lithium (1.56 M; 13.3 mL, 0.027 mol) in hexane is added dropwise to a solution of dimethyl methylphosphonate (3.69 g; 0.03 mol) in anhydrous THF (10 mL) cooled to −70° C. The mixture is stirred for 15 min before addition, dropwise, of a solution in anhydrous THF (10 mL) of methyl ester or of imidazolide, prepared as previously described.

Upon completion of the dripping step, the reaction mixture is kept, under stirring, for 1 h at −70° C. and then for 1 h at room: temperature. The mixture is then cooled to −10° C., and 1.8 mL of glacial acetic acid is added dropwise. The solvent is removed under vacuum, the residue is diluted with water, and the mixture is repeatedly extracted with dichloromethane (4×50 mL). The organic extracts are dried on sodium sulfate; after evaporation of the solvent, the residue is purified on silica gel, eluted with AcOEt to yield, as a colourless oil, 3.02 g of (R) (−)-dimethyl 3-(4-isobutyl)-2-oxobutan-1-phosphonate.

$[\alpha]_D$=−171° (c=1; $CH_3OH$); $^1$H-NMR ($CDCl_3$): σ.7.03 (s, 4H); 4.1-3.9 (dd, 2H, $J_1$=15 Hz, $J_2$=8 Hz); 3.8 (s; 3H); 3.70 (m, 1H); 3.65 (s, 3H); 2.55 (d, 2H, J=8 Hz); 1.75 (m, 1H); 1.50 (d, 3H, J=8 Hz); 0.85 (d, 6H, J=7 Hz).

Example 7

(R) (−) 2-(4-isobutylphenyl)-7-tert-butoxycarbonylamino-heptan-3-one

A solution of ethyl 5-tert-butoxycarbonylamino-2-ethoxycarbonyl-pentanoate (WO 94/10127) (1.59 g) in 3 mL of methanol is added to 8 mL of a 0.63 N solution of LiOH.$H_2O$ in water/methanol (1:1); the mixture is stirred for 12 h at room temperature. The mixture is diluted with 10 mL of a saturated solution of monosodium phosphate, and the excess of methanol is removed under vacuum. The mixture is extracted with ethyl acetate (2×10 mL); from the organic extracts, combined and dried on sodium sulfate, by evaporation of the solvent 1.4 g (4.8 mmol) of 5-tert-butoxycarbonylamino-2-ethoxycarbonyl-pentanoic acid are obtained.

To a solution of the acid (2.4 mmol) in 8 mL of anhydrous THF 0.27 g (2.4 mmol) of commercially available magnesium ethylate is then added, and the suspension is stirred at room temperature up to complete dissolution of the reagents to form the magnesium complex.

Then a solution of 0.3 g of (R) (−) 2-(4'-isobutylphenyl)-propionylimidazolide is added, and the mixture is stirred for 4 h at room temperature. The mixture is acidified by addition of a few mL of 50% aqueous AcOH, and the solvent is evaporated under vacuum. The residue is repartitioned between water and ethyl acetate to yield, after the usual processing, crude product (0.42 g) of ethyl (R,S)-2-[R-2-(4-isobutyl)-propionyl]-5-tert-butoxycarbonylamino-pentanoate, which is purified by flash chromatography.

A solution of 0.15 g of β-ketoester in DMSO/NaCl/$H_2O$ is then dealkoxydecarboxylated by heating to 135-145° C. to yield 0.08 g of (R) (−) 2-(4-isobutylphenyl)-7-tert-butoxycarbonylamino-heptan-3-one.

$[\alpha]_D$=−25 (c=1; $CH_3OH$); $^1$H NMR ($CDCl_3$); σ 7.25 (s, 4H); 6.35 (bs, 1H, CONH); 3.70 (q, 1H, J=8 Hz); 3.40 (m, 2H); 2.45 (d, 2H, J=7 Hz); 2.31 (m, 2H); 1.85 (m, 1H); 1.75=1.62 (m, 4H); 1.60 (d, 3H, J=7 Hz); 1.45 (s, 9H); 0.94 (d, 6H, J=7 Hz).

Example 8

Following the procedure of Example 7, but using as a starting material a monoester of a substituted malonic acid chosen in the group of:
methyl 2-carboxy-propionate;
methyl 2-carboxy-2-phenyl acetate;
methyl 2-carboxy-3-phenyl propionate;
methyl 2-carboxy-3(-pyrid-3-yl) propionate;
methyl 2-carboxy-3-cyclopentyl propionate;
the following β-ketoesters were obtained:
methyl(R',S')-2-[R-2-(4-isobutylphenyl)-propionyl] propionate;
methyl(R',S')-2-[R-2-(4-isobutylphenyl)-propionyl]-2-phenyl acetate;
methyl(R',S')-2-[R-2-(4-isobutylphenyl)-propionyl]-3-phenyl propionate;
methyl(R',S')-2-[R-2-(4-isobutylphenyl)-propionyl]-3-(pyrid-3-yl propionate;
methyl(R',S')-2-[R-2-(4-isobutylphenyl)-propionyl]-3-cyclopentyl propionate;
to obtain, after decarboxylation in DMSO/NaCl, the corresponding ketones:

R(−) 2-(4-isobutylphenyl)-pentan-3-one $[\alpha]_D$=−3.6 (c=1; $CH_3OH$); $^1$H-NMR ($CDCl_3$); σ 7.20 (d, 2H, J=7 Hz); 7.10 (d, 2H, J=7 Hz); 3.70 (q, 1H, J=8 Hz); 2.47 (d, 2H, J=7 Hz); 2.40 (q, 2H, J=7 Hz); 1.82 (m, 1H); 1.55 (d, 3H, J=7 Hz); 0.98 (d, 3H, J=7 Hz); 0.94 (d, 6H, J=7 Hz).

R(−) 2-(4-isobutylphenyl)-4-phenyl-butan-3-one $[\alpha]_D$=−48.5 (c=1; $CH_3OH$); $^1$H-NMR ($CDCl_3$); σ 7.35-7.18 (m, 5H); 7.15 (d, 2H, J=7 Hz); 7.05 (d, 2H, J=7 Hz); 3.72 (q, 1H, J=8 Hz); 3.65 (s, 2H); 2.42 (d, 2H, J=7 Hz); 1.80 (m, 1H); 1.60 (d, 3H, J=7 Hz); 0.93 (d, 6H, J=7 Hz).

R(−) 2-(4-isobutylphenyl)-5-phenyl-pentan-3-one $[\alpha]_D$=−40 (c=1.5; $CH_3OH$); $^1$H-NMR ($CDCl_3$); σ 7.37-7.20 (m, 5H); 7.10 (d, 2H, J=7 Hz); 7.00 (d, 2H, J=7 Hz); 3.70 (q, 1H, J=8 Hz); 2.88 (m, 2H); 2.75 (m, 2H); 2.45 (d, 2H, J=7 Hz); 1.82. (m, 1H) 1.63 (d, 3H, J=7 Hz); 0.95 (d, 6H, J=7 Hz).

R(−) 2-(4-isobutylphenyl)-5-(pyrid-3-yl)-pentan-3-one $[\alpha]_D$=−89 (c=1; $CH_3OH$); $^1$H-NMR ($CDCl_3$); σ 8.62 (m, 2H); 7.80 (m, 1H); 7.35. (m, 1H); 7.15 (d, 211, J=7 Hz); 7.08 (d, 2H, J=7 Hz); 5.35 (t, 2H; J=8 Hz); 5.05 (t, 2H, J=8112); 3.72 (q, 1H, J=8 Hz); 2.42. (d, 2H, J=7 Hz); 1.80 (m, 1H); 1.63 (d, 3H, J=7 Hz); 0.94 (d, 6H, J=7 Hz).

Example 9

(R,S) 1-phenyl-4-(4'-isobutylphenyl)-1,3-pentadione

A suspension of 0.55 g of magnesium ethylate in a solution of 1.61 g of benzoylacetic acid is stirred at room temperature, in an inert-gas atmosphere, up to total dissolution of the reagents. A solution of 0.6 g of (R,S)-2-(4'-isobutylphenyl)-propionylimidazolide is added, and stirring is continued overnight at room temperature. The mixture is brought to neutrality by addition of a few drops of 50% o aqueous AcOH, and is then evaporated to dryness under vacuum. The residue is repartitioned between water and ethyl acetate. The combined organic phases are dried on sodium sulfate, and evaporated to dryness. The residue is purified by flash chromatography to obtain 0.78 g of (R,S) 1-phenyl-4-(4'-isobutylphenyl)-1,3-pentadione.

$^1$H-NMR (CDCl$_3$); σ 7.90 (m, 2H); 7.65 (m, 1H); 7.52 (m, 2H); 7.20 (d, 2H, J=7 Hz) 7.12 (d, 2H, J=7 Hz); 3.77 (s, 2H); 3.68 (q, 1H J=8 Hz); 2.41 (d, 2H, J=7 Hz); 1.82 (m, 1H); 1.60 (d, 3H, J=7 Hz); 0.95 (d, 6H, J=7 Hz).

Example 10

Following the procedure of Example 9, and using a β-ketoacid chosen in the group of acetylacetic acid, 4-phenyl-3-oxo-butyrric acid or nicotinoylacetic acid, in place of benzoylacetic acid, the following are obtained:

(R,S) 5-(4'-isobutylphenyl)-hexan-2,4-dione $^1$H-NMR (CDCl$_3$); σ 7.20 (d, 2H, J=7 Hz); 7.12 (d, 2H, J=7 Hz); 3.75 (s, 2H); 3.65 (q, 1H, J=8 Hz); 2.40 (d, 2H, J=7 Hz); 2.10 (s, 3H); 1.82 (m, 1H); 1.62 (d, 3H, J=7 Hz); 0.94 (d, 6H, J=7 Hz).

(R,S) 1-phenyl-5-(4'-isobutylphenyl)-2,4-hexandione $^1$H-NMR (CDCl$_3$); σ 7.35-7.20 (m, 5H); 7.15 (d, 2H; J=7 Hz); 7.05 (d, 2H, J=7 Hz); 3.75 (s; 2H); 3.68 (q, 1H, J=8 Hz); 3.63 (s, 2H); 2.41 (d, 2H, J=7 Hz); 1.80 (m, 1H); 1.64 (d, 3H, J=7 Hz); 0.95 (d, 6H, J=7 Hz).

(R,S) 1-(pyrid-2-yl)-4-(4'=isobutylphenyl)-1,3-pentadione $^1$H-NMR (CDCl$_3$); σ 8.60 (m, 2H); 7.81 (m, 1H); 7.37 (m, 1H); 7.18 (d, 2H, J=7 Hz); 7.10 (d, 2H, J=7 Hz); 3.70 (q, 1H, J=8 Hz); 3.65 (s, 2H); 2.40 (d, 2H, J=7 Hz); 1.81 (m, 1H); 1.65 (d, 3H, J=7 Hz) 0.95 (d, 6H, J=7 Hz).

Example 11

(R,S) 2-(4'-isobutylphenyl)-3-oxo-butyl, methyl-sulfoxide

A solution of sodium hydride (21 mmol) in dry methylsulfoxide (5 mL) is heated at 60° C., in an inert-gas atmosphere, for 1 h. A solution of 2.2 g (10 mmol) of methyl 2-(4'-isobutylphenyl)-propionate in dry methylsulfoxide is dropped, and stirring is continued for 2 h at 60° C. The mixture is cooled at room temperature, brought to neutrality by addition of AcOH (0.25 mL), and diluted with diethyl ether. 1N HCl is added until pH=2 and CH$_2$Cl$_2$ and water are added. The two phases are debated and separated; the combined organic phases are dried on sodium sulfate, and evaporated to dryness. The residue is purified by flash chromatography to obtain 0.350 g of (R,S) 2-(4'-isobutylphenyl)-3-oxobutyl, methyl-sulfoxide.

$^1$H-NMR (CDCl$_3$); σ 7.14 (s, 4H); 3.85. (m, 2H); 3.52 (m, 1H); 2.65+2.54 (s, 3H, 2.47 (d, 2H, J=7 Hz); 1.87 (m, 1H); 1.43 (d, 3H, J=7 Hz); 0.92 (d, 6H, J=7 Hz).

According the same above described procedure and using the corresponding methyl ester of ketoprofen the following compound is obtained:

(R,S) 2-(3'-benzoylphenyl)-3-oxo-butyl, methyl-sulfoxide $^1$H-NMR (CDCl$_3$); σ 7.85-7.60 (m, 4H); 7.52-7.40 (m, 5H); 3.80 (m, 2H); 3.55 (m, 1H); 2.62+2.55 (s, 3H); 2.47 (d, 2H, J=7 Hz); 1.85 (m, 1H); 1.40 (d, 3H, J=7 Hz); 0.94 (d, 6H, J=7 Hz).

According the same above described procedure and using the methyl ester of the corresponding arylpropionic acids and methylsulfone (or phenylsulfone) instead of methylsulfoxide, the following compounds are obtained:

(R,S) 2-(4'-isobutylphenyl)-3-oxo-butyl, methyl-sulfone $^1$H-NMR (CDCl$_3$); σ 7.18 (s, 4H); 4.18 (m, 2H); 3.90 (m, 1H); 3.10 (s, 3H); 2.40 (d, 2H, J=7 Hz); 1.80 (m, 1H); 1.52 (d, 3H, J=7 Hz); 0.94 (d, 6H, J=7 Hz).

(R,S) 2-(3'-benzoylphenyl)-3-oxo-butyl, methyl-sulfone $^1$H-NMR (CDCl$_3$); σ 7.85-7.60 (m, 4H); 7.52-7.40 (m, 5H); 4.20 (m, 3H); 3.95 (m; 1H) 3.18 (s, 3H); 1.55 (d, 3H, J=7 Hz).

(R,S) 2-(3'-phenoxyphenyl)-3-oxo-butyl, methyl-sulfone $^1$H-NMR (CDCl$_3$); σ 7.25-7.38 (m, 2H); 7.15-7.05 (m, 2H); 7.02 (m, 2H); 6.70=6.60 (m, 2H); 6.55 (s, 1H); 4.21 (m, 3H); 4.15 (m, 1H); 3.20 (s, 3H); 1.58 (d, 3H, J=7 Hz). R;S) '2-(4'-isobutylphenyl)-3-oxo-butyl, phenyl-sulfone $^1$H-NMR (CDCl$_3$); σ 8.05 (m, 2H); 7.75 (m, 1H); 7.60 (m, 2H); 7.15 (s, 4H); 4.15 (m, 2H); 3.95 (m, 1H); 2.40 (d, 2H, J=7 Hz); 1.80 (m, 1H); 1.52 (d, 3H, J=7 Hz); 0.94 (d, 6H, J=7 Hz).

Example 12

(R)(−)-4-(4'-pyridyl)-2-[(4"-isobutyl)phenyl]butan-3-one

Diisopropylamine (0.17, mL; 1.21 mmol) and sodium hydride (60% in mineral-oil, 0.106 mg; 2.66. mmol) are dissolved in dry THF (20 mL) under nitrogen atmosphere; 4-pyridylacetic acid (0.166 g; 1.21 mmol) is added portionwise to the mixture and the mixture refluxed for 15'. After cooling at T=0°-4° C. by an ice-water bath, butyllithium (1.6 M in hexanes, 0.75 mL; 1.21 mmol)) is added to the mixture and, after 30', a solution of R(−)-2-(4'-isobutylphenyl)propionyl chloride (0.27 g; 1.21 mmol) in dry THF (10 mL) is added dropwise. At the end of the adding, the ice-water bath is removed and the solution is left under stirring overnight at room temperature. The solvent is evaporated under reduced pressure and the residue is diluted with diethyl ether (20 mL), washed with water (3×15 mL), dried over Na2SO4 and evaporated under vacuum to give a dark red oil which is dissolved in 6N HCl (5 mL). The solution is heated at reflux for 2 hours; after cooling at room temperature the solvents are evaporated under vacuum and the residue is purified by flash chromatography to give pure R(−)-4-(4'-pyridyl)-2-[(4"-isobutyl)phenyl]butan-3-one (0.25 g; 0.88 mmol) as pale yellow oil.

[α]$_D$=−148° (c=1; CHCl$_3$). $^1$H-NMR (CDCl$_3$): σ 8.54 (m, 2H); 7.15-6.90 (m, 6H); 3.85 (m, 1H); 3.72 (q, 2H, J=8 Hz); 2.51 (d, 3H, J=8 Hz); 1.87 (m, 1H); 1.45 (d, 2H, J=7 Hz) 0.92 (d, 6H, J=7 Hz).

Example 13

(S) (+) dimethyl 3-(3'-phenoxy-phenyl)-2-oxo-butan-1-phosphonate

Carbonyldiimidazole (0.18 g) is added to a solution of (S) 2-(3'-phenoxy-phenyl)-propionic acid (0.24 g) in anhydrous THF (5 mL) and is stirred for at least 1 h to form the corresponding imidazolide (Sol. A).

Separately, to a solution of dimethylphosphonoacetic acid (1.7 g) in anhydrous THF (25 mL) magnesium ethylate (0.5 g) is added, and the mixture is stirred for 3 h prior to rapid addition of the solution of imidazolide (Sol. A). The reaction mixture is stirred for 18 h at 25° C.

After evaporation of the solvent under vacuum, the residue is partitioned between ethyl acetate and 0.5 N aqueous HCl. The organic phase is washed with water, 5% aqueous sodium bicarbonate and water up to neutrality. After drying on $Na_2SO_4$, evaporation of the solvent and purification of the residue by flash chromatography on silica gel, 0.26 g of (S) (+) dimethyl 3-(3'-phenoxy-phenyl)-2-oxo-butyl-1-phosphonate are obtained.

$[\alpha]_D$=+125° (c=1; $CH_3OH$); $^1H$-NMR ($CDCl_3$); σ 7.25-7.32 (m, 2H); 7.15-7.05 (m, 2H); 7.03 (m, 2H); 6.70-6.65 (m, 2H); 6.50 (s, 1H); 4.15-3.9 (dd, 2H, $J_1$=15 Hz, $J_2$=8 Hz); 3.82 (s, 3H); 3.70 (m, 1H); 3.62 (s, 3H); 1.50 (d, 3H, J=8 Hz).

Example 14

(R) 2-[4-(1-oxo-2-isoindolinyl)phenyl]-3-oxo-valeramide

Carbonyldiimidazole (1.7 g) is added to a solution of 2.8 g of (R)-indoprofen in 15 mL of (anhydrous) THF, and is stirred for 2 h at room temperature to form the indoprofen imidazolide (Sol. A).

Separately, magnesium ethylate (2.3 g) is added, under stirring, to a solution of 4.2 g of the monoamide of malonic acid in 15 mL of THF. After the total dissolution of the reagents, the solution of the imidazolide is added, and the mixture is stirred for 24 h at room temperature.

After evaporation of the solvent under vacuum, the residue is divided between ethyl acetate and aqueous 0.5 N HCl. The organic phase is washed with water, 0.5% aqueous sodium bicarbonate and water up to neutrality. After drying on $Na_2SO_4$ evaporation of the solvent, and purification of the residue by flash chromatography on silica gel, 2.4 g of the amide of (R) 2-[4-(1-oxo-2-isoindolinyl)phenyl]-3-oxo-valeric acid is obtained.

$[\alpha]_D$=−46° (c=1; $CH_3OH$); $^1H$-NMR (DMSO-$d_6$); σ 7.70-7.55 (m, 3H); 7.45-7.30 (m, 3H); 7.15 (d, 2H, J=8 Hz); 5.55 (bs, 2H, $CONH_2$); 4.67 (s, 2H); 3.75 (m, 1H); 3.52 (s, 2H); 1.60 (d, 3H, J=8 Hz).

Example 15

(R) 2-(4-(1-oxo-2-isoindolinyl)phenyl]-3-oxo-valeronitrile

Following the procedure of Example 14, and substituting the monoamide of malonic acid with equimolecolar quantities of cyanacetic acid, (R) 2-(4-(1-oxo-2-isoindolinyl)phenyl]-3-oxo-valeronitrile is obtained.

$[\alpha]_D$=−21° (c=1; $CH_3OH$); $^1H$-NMR (DMSO-$d_6$); σ 7.71-7.50 (m, 3H); 7.45-7.30 (m, 3H); 7.18 (d, 2H, J=8 Hz); 4.65 (s, 2H); 3.72 (m, 1H); 3.63 (s, 2H); 1.55 (d, 3H, J=8 Hz).

The invention claimed is:

1. A method for the treatment of a disease that is selected from the group consisting of psoriasis, rheumatoid arthritis, ulcerative cholitis, acute respiratory distress syndrome (ARDS), glomerulonephritis, and for the prevention and the treatment of damage caused by ischemia and reperfusion, comprising administering to a subject in need thereof an effective amount of a composition comprising (R,S)-1-Arylethylketone compounds of formula I, or their single (R) or (S) enantiomers:

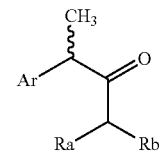

(I)

wherein

Ar represents phenyl, optionally substituted by one to three substituents, which are the same or different from one another and selected from:

($C_1$-$C_4$)alkyl, benzoyl, benzoyloxy, isopropylsulfonyloxy, 2-ethylphenylsulfonylamino, phenoxy, 1-oxo-2-isoindolinyl;

Ra and Rb are independently chosen from the group consisting of hydrogen; linear or branched $C_1$-$C_6$ alkyl; phenyl; ($C_1$-$C_4$)-alkylphenyl; carboxyl; carboxy esters of formula $CO_2R''$, wherein R" is the residue of a linear or branched $C_1$-$C_6$ aliphatic alcohol; phosphonates of formula $PO(OR'')_2$ wherein R" is the residue of a linear or branched $C_1$-$C_6$ aliphatic alcohol; 2,3 or 4-pyridyl; a group of formula X—$(CH_2)_n$—Z, wherein X is a CO, SO or $SO_2$ group, Z is H, phenyl or 2-, 3- or 4-pyridyl and n is zero or an integer from 1 to 3.

2. The method according to claim 1, wherein

Ar is selected from the group consisting of phenyl substituted by one to three substituents, which are the same or different from one another and selected from the group consisting of ($C_1$-$C_4$) alkyl, benzoyl, 1-oxo-2-isoindolinyl; and Ra and Rb are independently chosen from the group consisting of hydrogen, linear or branched $C_1$-$C_6$ alkyl, phenyl, ($C_1$-$C_4$)-alkylphenyl, 2-, 3- or 4-pyridyl, a group of formula X—$(CH_2)_n$-Z, wherein X is a CO, Z is H and n equals zero.

3. The method according to claim 1, wherein

Ar is a phenyl substituted by one substituent selected from the group consisting of isobutyl, benzoyl and 1-oxo-2-isoindolinyl; and Ra and Rb are independently chosen from the group consisting of hydrogen, phenyl, 2-, 3- or 4-pyridyl and a group of formula X—$(CH_2)_n$-Z, wherein X is a CO, Z is H and n equals zero.

4. The method according to claim 1, wherein the compound is selected from the group consisting of:

methyl (R)(−)-4-[(4'-isobutyl)phenyl]-3-oxopentanoate;
methyl (S)(+)-4-[(4'-isobutyl)phenyl]-3-oxopentanoate;
(R,S) 4-[(4'-isobutyl)phenyl]-3-oxopentanoic acid;
methyl (R)(−)-4-[(3'-benzoyl)phenyl]-3-oxopentanoate
(R)(−)-3-[(4'-isobutyl)phenyl]butan-2-one;
(S)(+)-3-[(4'-isobutyl)phenyl]butan-2-one;
(R)(−)-3-[(3'-benzoyl)phenyl]butan-2-one;
(R)(−)-dimethyl 3-(4-isobutylphenyl)-2-oxobutan-1-phosphonate;
(S)(+)-dimethyl 3-(3'-phenoxy-phenyl)-2-oxo-butyl-1-phosphonate;
(R)(−)-2-(4-isobutylphenyl)-pentan-3-one;
(S)(+)ethyl-4-[(3'-benzoyl)phenyl]-3-oxopentanoate;
(S)(+)-3-[(3'-benzoyl)phenyl]butan-2-one;
(R)(−)-2-(4-isobutylphenyl)-4-phenyl-butan-3-one;
(R)(−)-2-(4-isobutylphenyl)-5-phenyl-pentan-3-one;

(R)(−)-2-(4-isobutylphenyl)-5-(pyrid-3-yl)-pentan-3-one;
(R)(−) methyl 4-[(4'-benzoyloxy)phenyl]-3-oxopentanoate;
(R)(−) methyl 4-[(4'-isopropylsulfonyloxy)phenyl]-3-oxopentanoate;
(R)(−) methyl-4-1-[4'-(2"-ethyl)phenylsulfonylamino]phenyl]-3-oxopentanoate;
(R,S) 5-(4'-isobutylphenyl)-hexan-2,4-dione;
(R,S) 1-phenyl-5-(4'-isobutylphenyl)-2,4-hexandione;
(R,S) 1-(pyrid-2-yl)-4-(4'-isobutylphenyl)-1,3-pentadione;
(R,S) 2-(4'-isobutylphenyl)-3-oxo-butyl, methyl-sulfoxide;
(R,S) 2-(3'-benzoylphenyl)-3-oxo-butyl, methyl-sulfoxide;
(R,S) 2-(4'-isobutylphenyl)-3-oxo-butyl, methyl-sulfone;
(R,S) 2-(3'-benzoylphenyl)-3-oxo-butyl, methyl-sulfone;
(R,S) 2-(3'-phenoxyphenyl)-3-oxo-butyl, methyl-sulfone;
(R,S) 2-(4'-isobutylphenyl)-3-oxo-butyl, phenyl-sulfone;
(R)(−)-4-(4'-pyridyl)-2-[(4"-isobutyl)phenyl]butan-3-one.

5. The method according to claim 1, wherein the compound is selected from the group:
(R)(−)-3-[(4'-isobutyl)phenyl]butan-2-one;
(S)(+)-3-[(4'-isobutyl)phenyl]butan-2-one;
(R)(−)-3-[(3'-benzoyl)phenyl]butan-2-one;
(R)(−)-2-(4-isobutylphenyl)-pentan-3-one;
(S)(+)-3-[(3'-benzoyl)phenyl]butan-2-one;
(R)(−)-2-(4-isobutylphenyl)-4-phenyl-butan 3-one;
(R)(−)-2-(4-isobutylphenyl)-5-phenyl-pentan-3-one;
(R)(−)-2-(4-isobutylphenyl)-5-(pyrid-3-yl)-pentan-3-one;
(R,S) 5-(4'-isobutylphenyl)-hexan-2,4-dione;
(R)(−)-4-(4'-pyridyl)-2-[(4"-isobutyl)phenyl]butan-3-one;
(R)-2-[4-(1-oxo-2-isoindolinyl)phenyl]-3-oxo-valeramide.

6. The method according to claim 1, wherein the steric configuration of the carbon atom to which the residue Ar is bound corresponds to the enantiomer (R).

7. The method according to claim 1, wherein said composition further comprises a pharmaceutically acceptable carrier.

8. A method for treating glomerulonephritis and for treating or preventing damage caused by ischemia and reperfusion, comprising administering to a subject in need thereof an effective amount of a composition comprising (R,S)-1-Arylethylketone compounds of formula I, or their single (R) or (S) enantiomers:

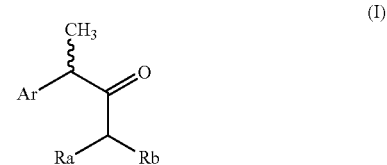

(I)

wherein
Ar represents phenyl, optionally substituted by one to three substituents, which are the same or different from one another and selected from:
($C_1$-$C_4$)alkyl, benzoyl, benzoyloxy, isopropylsulfonyloxy, 2-ethylphenylsulfonylamino, phenoxy, 1-oxo-2-isoindolinyl;
Ra and Rb are independently chosen from the group consisting of hydrogen; linear or branched $C_1$-$C_6$ alkyl; phenyl; ($C_1$-$C_4$)-alkylphenyl; carboxyl; carboxy esters of formula $CO_2R''$, wherein R'' is the residue of a linear or branched $C_1$-$C_6$ aliphatic alcohol; phosphonates of formula $PO(OR'')_2$ wherein R'' is the residue of a linear or branched $C_1$-$C_6$ aliphatic alcohol; 2,3 or 4-pyridyl; a group of formula X—$(CH_2)_n$—Z, wherein X is a CO, SO or $SO_2$ group, Z is H, phenyl or 2-, 3- or 4-pyridyl and n is zero or an integer from 1 to 3.

* * * * *